United States Patent
Imshenetskiy et al.

(10) Patent No.: US 10,556,846 B2
(45) Date of Patent: Feb. 11, 2020

(54) METHOD OF PRODUCING CONCENTRATE OF AROMATIC HYDROCARBON FROM LIQUID HYDROCARBON FRACTIONS, AND INSTALLATION FOR IMPLEMENTING SAME

(71) Applicant: NGT GLOBAL AG.

(72) Inventors: Vladimir Vladislavovich Imshenetskiy, Gorki Leninskie (RU); Denis Vasilyevich Pchelintsev, Moscow (RU); Iosif Izrailevich Lishchiner, Moscow (RU); Olga Vasilyevna Malova, pos. Gorki Leninskie (RU); Andrey Leonidovich Tarasov, Moscow (RU)

(73) Assignee: NGT Global AG, Zug (CH)

( * ) Notice: Subject to any disclaimer, the term of this patent is extended or adjusted under 35 U.S.C. 154(b) by 0 days.

(21) Appl. No.: 15/502,956

(22) PCT Filed: Aug. 10, 2015

(86) PCT No.: PCT/RU2015/000496
§ 371 (c)(1),
(2) Date: Feb. 9, 2017

(87) PCT Pub. No.: WO2016/024883
PCT Pub. Date: Feb. 18, 2016

(65) Prior Publication Data
US 2017/0233311 A1    Aug. 17, 2017

(30) Foreign Application Priority Data
Aug. 12, 2014    (RU) .................... 2014133053

(51) Int. Cl.
*C07C 2/66*    (2006.01)
*B01J 8/00*    (2006.01)
(Continued)

(52) U.S. Cl.
CPC ............. *C07C 2/864* (2013.01); *C10G 3/49* (2013.01); *C10G 11/05* (2013.01); *C10G 35/095* (2013.01);
(Continued)

(58) Field of Classification Search
CPC ..................... C07C 2/66; B01J 8/00
(Continued)

(56) References Cited

U.S. PATENT DOCUMENTS 3,702,886 A    11/1972    Argauer
3,756,942 A    9/1973    Cattanach
(Continued)

FOREIGN PATENT DOCUMENTS

RU    2160161    12/2000
RU    2284343    9/2006
(Continued)

OTHER PUBLICATIONS

WO2016024883 ISR—Translation.
(Continued)

*Primary Examiner* — Thuan D Dang
(74) *Attorney, Agent, or Firm* — Glen P. Belvis; Belvis Law, LLC.

(57) ABSTRACT

The invention relates to the field of petrochemistry and petroleum refining, and more-specifically to methods and devices for producing a concentrate of aromatic hydrocarbons from liquid hydrocarbon fractions, which involve feeding initial components into a mixer, heating said components, feeding same to a reactor in which the heated components are converted into aromatic hydrocarbons in the presence of a catalyst, separating same into liquid and gas phases, feeding the gas phase into the mixer, and feeding the liquid phase into a rectification column, from which an aromatic hydrocarbon concentrate is collected, and can be
(Continued)

used in petroleum refining and in petrochemistry for producing a concentrate aromatic hydrocarbons. According to the invention, methanol is additionally fed into the mixer. Hydrocarbon components which remain in the rectification column following collection are at least partially fed into the mixer. The liquid phase is additionally separated into liquid hydrocarbons and water, the liquid hydrocarbons are fed into the rectification column, and the water is removed. The composition of the liquid aromatic hydrocarbons, which are fed into the rectification column, is measured. In accordance with the results of the measurements, the flow rate of the initial components fed into the mixer is adjusted, and/or the temperature of the rectification column is adjusted. A proposed installation carries out the said method. The achieved technical result consists in increasing the efficiency of producing concentrates of aromatic hydrocarbons, and in increasing the content of alkylbenzenes, particularly xylenes.

10 Claims, 3 Drawing Sheets

(51) Int. Cl.
  *C07C 2/86* (2006.01)
  *C10G 35/095* (2006.01)
  *C10G 3/00* (2006.01)
  *C10G 11/05* (2006.01)
(52) U.S. Cl.
  CPC ...... *C07C 2529/04* (2013.01); *C10G 2400/30* (2013.01); *Y02P 30/20* (2015.11)
(58) Field of Classification Search
  USPC .................. 585/467, 469; 422/234, 235, 236
  See application file for complete search history.

(56) References Cited

U.S. PATENT DOCUMENTS

| | | | |
|---|---|---|---|
| 3,911,041 A | 10/1975 | Kaeding et al. |
| 3,941,871 A | 3/1976 | Dwyer et al. |
| 4,159,282 A | 6/1979 | Olson et al. |
| 4,211,640 A | 7/1980 | Garwood et al. |
| 4,227,992 A | 10/1980 | Garwood et al. |
| 4,356,338 A | 10/1982 | Young |
| 4,456,527 A | 6/1984 | Buss et al. |
| 4,463,204 A | 7/1984 | Liu |
| 4,465,886 A | 8/1984 | Rodewald |
| 4,499,314 A | 2/1985 | Seddon et al. |
| 4,523,049 A | 6/1985 | Jones et al. |
| 4,554,260 A | 11/1985 | Pieters et al. |
| 4,590,321 A | 5/1986 | Chu |
| 4,720,602 A | 1/1988 | Chu |
| 4,853,202 A | 8/1989 | Kuznicki |
| 4,899,011 A | 2/1990 | Chu |
| 4,963,337 A | 10/1990 | Zones |
| 5,108,579 A | 4/1992 | Casci |
| 5,173,461 A | 12/1992 | Absil et al. |
| 5,178,748 A | 1/1993 | Casci et al. |
| 5,306,411 A | 4/1994 | Mazanec et al. |
| 5,321,183 A | 6/1994 | Chang et al. |
| 5,362,697 A | 11/1994 | Fung et al. |
| 5,365,003 A | 11/1994 | Chang et al. |
| 5,453,554 A | 9/1995 | Cheng et al. |
| 5,498,814 A | 3/1996 | Chang et al. |
| 5,516,736 A | 5/1996 | Chang et al. |
| 5,536,894 A | 7/1996 | Degnan et al. |
| 5,557,024 A | 9/1996 | Cheng et al. |
| 5,935,897 A | 8/1999 | Trubenbach et al. |
| 5,993,642 A | 11/1999 | Mohr et al. |
| 6,046,372 A | 4/2000 | Brown et al. |
| 6,063,724 A | 5/2000 | Resasco et al. |
| 6,096,193 A | 8/2000 | Resasco et al. |
| 6,143,166 A | 11/2000 | Nacamuli |
| 6,413,898 B1 | 7/2002 | Faber et al. |
| 6,423,879 B1 | 7/2002 | Brown et al. |
| 6,504,072 B1 | 1/2003 | Brown et al. |
| 6,635,792 B2 | 10/2003 | Choi et al. |
| 6,906,232 B2 | 6/2005 | Levin et al. |
| 6,995,111 B2 | 2/2006 | Levin et al. |
| 7,026,263 B2 | 4/2006 | Le Van Mao |
| 7,078,578 B2 | 7/2006 | Janssens et al. |
| 7,122,492 B2 | 10/2006 | Ou et al. |
| 7,122,493 B2 | 10/2006 | Ou et al. |
| 7,164,052 B2 | 1/2007 | Carati et al. |
| 7,208,442 B2 | 4/2007 | Xu et al. |
| 7,419,930 B2 | 9/2008 | Carati et al. |
| 7,700,816 B2 | 4/2010 | Xu et al. |
| 7,923,399 B2 | 4/2011 | Long et al. |
| 8,226,740 B2 | 7/2012 | Chaumonnot et al. |
| 8,338,655 B2 | 12/2012 | Chang et al. |
| 9,040,003 B2 | 5/2015 | Andersen et al. |
| 2008/0027255 A1 | 1/2008 | Blessing et al. |
| 2008/0300434 A1 | 12/2008 | Cortright et al. |
| 2008/0300435 A1 | 12/2008 | Cortright et al. |
| 2009/0288990 A1 | 11/2009 | Xie et al. |
| 2010/0145127 A1 | 6/2010 | Xie et al. |
| 2013/0066126 A1 | 3/2013 | Jana |
| 2013/0317269 A1 | 11/2013 | Nesterenko et al. |
| 2014/0018592 A1 | 1/2014 | Chen et al. |
| 2014/0058180 A1 | 2/2014 | Klingelhofer et al. |
| 2014/0100404 A1 | 4/2014 | Narula et al. |
| 2014/0256010 A1 | 9/2014 | Narula et al. |
| 2014/0273146 A1 | 9/2014 | Narula et al. |
| 2014/0322781 A1 | 10/2014 | Narula et al. |
| 2017/0001922 A1 | 1/2017 | Lishchiner et al. |
| 2017/0007992 A1 | 1/2017 | Lishchiner et al. |
| 2017/0145317 A1 | 5/2017 | Lischiner et al. |
| 2017/0233311 A1 | 8/2017 | Vladislavovich et al. |

FOREIGN PATENT DOCUMENTS

| | | |
|---|---|---|
| RU | 2289477 | 12/2006 |
| RU | 2294799 | 3/2007 |
| RU | 2320631 | 3/2008 |
| RU | 2323777 | 5/2008 |
| RU | 2333033 | 9/2008 |
| RU | 2349567 | 3/2009 |
| RU | 2349568 | 3/2009 |
| RU | 2350591 | 3/2009 |
| RU | 2350592 | 3/2009 |
| RU | 2354638 | 5/2009 |
| RU | 2354639 | 5/2009 |
| RU | 2362760 | 7/2009 |
| RU | 2391135 | 6/2010 |
| RU | 2009101606 | 7/2010 |
| RU | 2429910 | 9/2011 |
| RU | 2433863 | 11/2011 |
| RU | 2440189 | 1/2012 |
| RU | 2446135 | 3/2012 |
| RU | 2010135608 | 3/2012 |
| RU | 2454388 | 6/2012 |
| RU | 2458898 | 8/2012 |
| RU | 2466976 | 11/2012 |
| RU | 2477656 | 3/2013 |
| RU | 2495017 | 10/2013 |
| RU | 2509759 | 3/2014 |
| RU | 2518091 | 6/2014 |
| RU | 2544241 | 3/2015 |
| WO | WO 2008/109877 | 9/2008 |
| WO | WO 2015/115932 | 8/2015 |
| WO | WO 2015/147700 | 10/2015 |
| WO | WO 2016/024883 | 2/2016 |
| WO | WO 2017/155424 | 9/2017 |

OTHER PUBLICATIONS

WO2016024883 PCT-RU15.
WO2016024883 Written Opinion.

(56) References Cited

OTHER PUBLICATIONS

May 2004, Yuan, Alkylation of benzene with ethanol ver ZSM-5 Catalyst (Indian Journal of Chemical Technology, vol. 1, May 2004, pp. 337-345).
EPO, EP 14 881 043.5 Report.
May 15, 2018, EPO, EP 15 741 108.3 Report.
May 26, 2017, EPO, EP 15 741 108.3 Extended Report.
Oct. 26, 2017, EPO, EP 15 768 758.3 Report.
Feb. 12, 2018, EPO, EP 15 831 280.1 Report.
Feb. 13, 2017, RU patent Office, 201600533 Office Action.
Oct. 21, 2016, RU patent Office, 201600532 Office Action.
Oct. 21, 2016, RU patent Office, 201600667 Office Action.
Apr. 28, 2018, RU patent Office, 201700105 Office Action.

| Description of Product | Sulfur Fraction, % by Weight |
|---|---|
| Pyrolysis gasoline | 0.0063 |
| Pyrolysis gasoline hydrogenation product | 0.0032 |
| Product of refining pyrolysis gasoline with methanol (1:1) | 0.001 |

Figure 3

|  | Prototype Example 1 | Prototype Example 4 | Invention Example 1 ("Crude" Pyrolysis Condensate Hour 3) | Invention Example 2 (Hydrotreated "Crude" Pyrolysis Condensate Hour 3) |
|---|---|---|---|---|
| Composition of Hydrocarbon Feedstock | | | | |
| Nonaromatics, % by wt. | 34.3 | 34.3 | 31.7 | 25 |
| olefins, incl. dienes and aromatic olefins | None | None | 10.7 | None |
| Aromatics, % by wt. | 65.7 | 65.7 | 68.3 | 75 |
| benzene | Not specified | | 40.7 | 39 |
| toluene | Not specified | | 12.6 | 16.6 |
| xylenes and ethylbenzene | Not specified | | 2.7 | 7.3 |
| Methanol in mixture by weight | 0 | 0 | 49 | 49 |
| Conversion Products | | | | |
| $H_2$, $C_1$–$C_2$, % by wt. | 13.5 | 12.6 | 1.5 | 1.6 |
| LPG ($C_3$–$C_4$), % by wt. | 30.3 | 31.6 | 9 | 11 |
| AHCC ($C_{5+}$), % by wt. | 56.2 | 55.8 | 62 | 59.9 |
| Water, % by wt. | 0 | 0 | 27.5 | 27.5 |
| AHCC Composition | | | | |
| $C_5$–$C_6$ nonaromatics | 1.9 | 2.6 | 9.5 | 9.7 |
| $C_6$–$C_8$ aromatics | 87.3 | 83.7 | 66.7 | 63.8 |
| benzene | Not specified | | 15.4 | 12.9 |
| toluene | Not specified | | 23.7 | 24.4 |
| xylenes and ethylbenzene | Not specified | | 27.6 | 26.5 |
| $C_{9+}$ aromatics | 10.8 | 13.7 | 23.8 | 26.5 |
| T, °C | 420 | 500 | 450 | 450 |
| P, MPa | 2.7 | 2.7 | 1 | 1 |
| W, kg/kg·h$^{-1}$ (in terms of feed hydrocarbons) | 2.7 | 2.7 | 1 | 1 |
| Weight ratio of aromatics in feedstock to aromatics in conversion product, % | 84 | 83 | 164 | 144 |

Figure 4

METHOD OF PRODUCING CONCENTRATE OF AROMATIC HYDROCARBON FROM LIQUID HYDROCARBON FRACTIONS, AND INSTALLATION FOR IMPLEMENTING SAME

This application is a US nationalization pursuant to 35 U.S.C. § 371 of PCT/RU2015/000496 filed Aug. 10, 2015, which claims priority to RU Patent Application Serial No. 2014133053, filed August 12.

AREA OF TECHNOLOGY TO WHICH THE INVENTION BELONGS

The invention relates to the field of petrochemistry and petroleum refining, and more specifically to methods and devices for producing aromatic hydrocarbon concentrate (AHCC) from liquid hydrocarbon fractions, in which feedstock is fed to a mixer, heated, fed to a reactor in which the heated feedstock is converted in the presence of a catalyst to aromatic hydrocarbons and separated into liquid and gaseous phases, the gaseous phase is fed to a mixer, and the liquid phase to a rectification column, from which the AHCC is collected and may be used in petroleum refining and petrochemistry to produce AHCC for use as a component with elevated knock resistance of internal combustion engine gasolines and for further refining to marketable aromatic hydrocarbons.

"Marketable aromatic hydrocarbons" means selected hydrocarbons and fractions thereof (benzene, toluene, p-xylene, o-xylene, etc.) meeting trade specifications, usually described in State Standards [GOST] or Technical Specifications [TU] for products.

As liquid hydrocarbon fractions that serve as feedstock, the process uses byproducts of oil and gas chemical processes, such as light aliphatic and alicyclic hydrocarbon fractions, products of gas stripping and stabilization of crude hydrocarbons, pyrolysis condensates, and benzene and benzene-toluene fractions of various origins.

In this specification, "methanol" is intended to mean methanol or crude methanol.

The refining of feed hydrocarbons often raises the issue of recycling various hydrocarbon fractions that are byproducts of various processes. In particular, such fractions may include:
- natural gas liquids of various origin, for example, gases from catalytic cracking and stabilization of hydrocarbons from various processes, etc.,
- benzene or benzene-toluene containing fractions, for example, liquid pyrolysis products
- benzene fractions, for example, those separated from reformates so as to reduce the benzene content in gasolines.

There is a problem of diversifying the feedstock for the production of gasolines, marketable aromatic hydrocarbons, and other products to more available products of gas refining such as natural gas liquids, condensed hydrocarbon gases, and methanol.

The aforementioned products can be refined to the desired gasoline component, consisting mainly of $C_7$-$C_9$ aromatic hydrocarbons. The proportion of aromatic hydrocarbons in gasolines, pursuant to technical regulations for the production of class-four and -five gasolines (according to the classification of the EurAsEC Technical Regulation, "Safety Requirements for Automotive Gasoline, Diesel Fuel, and Home Heating Oil"), must not exceed 35% by volume or ~40% by weight.

Experience has shown that it is difficult to make gasolines with RON=95/98 (research octane number pursuant to GOST, included in the grade of gasoline after the letter "I," for example, "AI-98") with less than 40% aromatic hydrocarbon content by weight. To compensate for the shortage of aromatic hydrocarbons, refineries are forced to operate reforming units in "stricter" modes resulting in elevated gas production.

The invention is aimed at solving the problem of balancing the gasoline pool (component stocks for gasoline compounding) with respect to $C_{7+}$ aromatic hydrocarbons by producing aromatic hydrocarbons using byproducts of other processes and cheaper and more available products of gas refining (natural gas liquids, methanol) as well as using the aforementioned petrochemical process byproducts to produce AHCC used as feedstock for the production of marketable aromatic hydrocarbons (for example, toluene, xylenes).

TECHNOLOGICAL LEVEL OF THE METHOD

In one respect he present invention relates to methods of producing AHCC from liquid hydrocarbon fractions, in which feedstock is fed to a mixer, the mixed feedstock is heated and fed to a reactor in which the heated feedstock is converted in the presence of a zeolite catalyst to aromatic hydrocarbons, the resulting product is separated into liquid and gaseous phases, the gaseous phase is fed to a mixer, and the liquid phase is fed to a rectification column, from which the AHCC is collected.

Such a method is described in U.S. Pat. No. 6,635,792B2, published Oct. 21, 2003. This method is the closest in technical essence and is chosen as a prototype for the claimed invention as a method.

The disadvantage of this method is the low efficiency of AHCC production and the low concentration of alkylbenzenes, in particular xylenes. In fact, in this method nonaromatic hydrocarbons are cracked to produce $C_1$-$C_4$ hydrocarbons, while aromatic hydrocarbons are partially dealkylated, that is, there is no increment in aromatic hydrocarbons. In this method the percentage of aromatic hydrocarbons in the yield is only 82-83% of the weight of aromatic hydrocarbons in the feedstock (according to the prototype examples, the feedstock contains 65% aromatic hydrocarbons by weight, while the conversion products contain 55-60% aromatic hydrocarbons by weight). Moreover, the resulting AHCC is found to contain a high concentration of undesirable benzene and insignificant $C_7$-$C_8$ aromatic hydrocarbons.

DISCLOSURE OF THE INVENTION AS A METHOD

The present invention has the principal aim of offering a method of producing AHCC from liquid hydrocarbon fractions that helps to improve AHCC production and to increase the concentration of alkylbenzenes, in particular xylenes.

The technical objective is accomplished by:
- feeding additional methanol to the mixer,
- heating the mixed feedstock to a gaseous state with full homogenization,
- feeding at least part of the hydrocarbon components remaining in the rectification column after collection to the feedstock mixer,
- additionally separating the liquid phase into liquid hydrocarbons and water, and feeding the liquid hydrocarbons to the rectification column while diverting the water, measuring the composition of liquid aromatic hydrocarbons fed to the rectification column, and based on the results of measurement of the liquid aromatic hydrocarbon composition adjusting the ratio between the feedstock components fed to the mixer, and/or the temperature of the bottom of the rectification column.

These advantageous characteristics make it possible to improve the efficiency of AHCC production and to increase the concentration of alkylbenzenes, in particular xylenes.

Indeed, even crude pyrolysis condensate that has not undergone liquid-phase hydrogenation of dienes and styrenes when used in the mixture with methanol does not form deposits on heat exchanger walls when the mixture is heated, and the presence of methanol inhibits radical oligomerization of dienes and aromatic olefins present in the feedstock when heated. Also, during co-conversion of hydrocarbons and methanol on zeolite catalysts, coke is deposited less rapidly on the catalyst surface, which is also associated with the presence of water vapor (as noted for example in patent RU 2030376) formed during methanol conversion and with the high temperature of the process, which is higher than the temperature at which the rate of radical oligomerization of dienes is lower than the rate of their depolymerization.

The presence of benzene and toluene in the conversion mixture leads to their alkylation with the formation of higher alkylbenzenes. The alkylating agent here is methanol. The presence of m-xylene in the conversion mixture leads to disproportionation of m-xylene with the formation of a xylene mixture with a near-equilibrium composition.

The hydrocarbon fraction collected from the bottom of the column during co-conversion of hydrocarbons with methanol actually consists primarily of alkylbenzenes, including xylenes.

Light aliphatic hydrocarbons, benzene, and toluene collected from the top of the column, when recycled to the start of the process (mixing of feedstock with methanol) are also partly converted to higher aromatic hydrocarbons. This permits the recycle of said fractions to increase the yield of alkylbenzenes. Aromatic hydrocarbons contained in the recycle also participate in disproportionation and alkylation reactions, leading to the formation of higher aromatic hydrocarbons.

The composition of xylenes in the conversion product is close to equilibrium with a predominance of m-xylene. Disproportionation reactions occur on the catalyst, which permits recycling to the head of the process not only of benzene and toluene in a mixture with aliphatic hydrocarbon, but also, for example, of meta-xylene for conversion to the xylene mixture containing ortho- and para-xylenes.

The advantageous characteristic of measuring the composition of liquid aromatic hydrocarbons that are fed to the rectification column and, based on the measurement results, adjusting the ratio between feedstock components fed to the mixer and/or the temperature of the rectification column makes it possible to adjust the process parameters precisely to maximize the yield of the desired product.

A variant of the invention exists in which methanol is fed to the mixer to form a mixture in which methanol makes up 20-70% by weight.

This advantageous characteristic makes it possible to increase the aromatic hydrocarbon concentration and the concentration of alkylbenzenes, in particular xylenes.

A variant of the invention exists in which, when the composition of liquid aromatic hydrocarbons fed to the rectification column is measured, the benzene concentration and the total concentration of aromatic hydrocarbons, consisting primarily of methylbenzenes, are determined; if the ratio of benzene concentration to total aromatic hydrocarbon concentration rises or falls, the flow rate of feedstock components fed to the mixer and/or the temperature of the rectification column is adjusted so that the benzene content of the mixture fed to the column with respect to the total aromatic hydrocarbon content of the mixture fed to the column is in the range of 8-30% by weight.

This advantageous characteristic makes it possible to adjust the process parameters precisely to maximize the yield of the desired product. Indeed, the composition of the equilibrium methylbenzene mixture depends on the ratio of the number of methyl groups to the number of phenyl groups. As the ratio of the total methyl groups to the total phenyl groups increases above 1.7, the molar ratio of xylenes remains practically unchanged, but the concentration of trimethylbenzenes, tetramethylbenzenes, etc. right up to hexamethylbenzenes increases. These heavy aromatic hydrocarbons have limited applications. Although the composition of methylbenzenes in the conversion product is not at equilibrium, the rule of growth in the number of methyl groups to the number of phenyl groups in the aromatic fraction as the methanol feed is increased with respect to the hydrocarbons still applies. If the target product of the process is toluene, which is a valuable component of gasolines, it is best to reduce the methanol/hydrocarbon ratio to a minimum.

A variant of the invention exists in which the flow rate of feedstock components fed to the mixer is adjusted by altering the methanol flow rate.

This advantageous characteristic makes it possible to control the process by adjusting the methanol flow rate in particular.

A variant of the invention exists in which the flow rate of feedstock components fed to the mixer is adjusted by altering the hydrocarbon fraction flow rate.

This advantageous characteristic makes it possible to control the process by adjusting the hydrocarbon fraction flow rate in particular.

A variant of the invention exists in which, after heating mixed components to a temperature at which hydrocarbons with boiling points below 250° C. at standard conditions preferentially evaporate, tars (products of radical oligomerization of dienes and aromatic olefins present in the feedstock) are separated using a centrifugal tar separator.

This advantageous characteristic makes it possible to separate and remove undesirable products.

A variant of the invention exists in which the liquid aromatic hydrocarbon composition is measured using a flow chromatograph.

This advantageous characteristic makes it possible to measure the liquid aromatic hydrocarbon composition using a precise and tested method.

The combination of essential features of the claimed invention is unknown from the technological level for methods with similar purposes, which supports the conclusion that the invention as a method meets the novelty criterion.

TECHNOLOGICAL LEVEL OF THE INSTALLATION

In another respect, the present invention elates to an installation for producing AHCC from liquid hydrocarbon fractions, including a mixer of feedstock components whose output is connected to the input of a mixed component heating unit, whose output is connected to the input of a reactor in which the heated components undergo conversion in the presence of a catalyst to aromatic hydrocarbons, whose output is connected to the input of a unit for separating the resulting product into liquid and gaseous phases, whose first, gas-phase, output is connected to the first input of a feedstock component mixer and whose second, liquid-phase, output is connected to the input of a rectification column, from whose first output the aromatic hydrocarbon concentration is collected.

Such an installation is described in U.S. Pat. No. 6,635, 792B2, published Oct. 21, 2003. This installation is most similar in technical essence and has been selected as the prototype for the claimed invention as a device.

The disadvantage of the prototype invention is its low efficiency in AHCC production and low concentration of alkylbenzenes, in particular xylenes. Indeed, this installation cracks nonaromatic hydrocarbons to produce $C_1$-$C_4$, while partially dealkylating aromatic hydrocarbons, i.e., there is no increment in aromatic hydrocarbons. The percentage of aromatic hydrocarbons at the output of this installation is only about 82-83% of the content of the input feedstock, but the proportion of nonaromatic hydrocarbons in the $C_{5+}$ fraction of the conversion product is only 1-1.8% by weight. At the same time the conversion products are found to contain a high concentration of undesirable benzene and an insufficient concentration of $C_7$-$C_9$ alkylbenzenes.

DISCLOSURE OF THE INVENTION AS AN INSTALLATION

The present invention also has the goal of offering an installation for producing AHCC from liquid hydrocarbon fractions that makes it possible to at least reduce the aforementioned disadvantages, specifically, the efficiency of AHCC production to be increased and the concentration of alkylbenzenes, in particular xylenes, to be increased.

To achieve this goal, the feedstock component mixer has a second methanol feed input, adapted for connection to a methanol feed unit. The rectification column has a second output for components remaining after AHCC collection, connected to the third input of the feedstock component mixer. The unit for separating the resulting product into liquid and gaseous phases additionally has a module for separating the liquid phase into liquid hydrocarbons and water, connected to the input of the rectification column and having an output for removal of water.

The installation additionally includes a unit for measuring the composition of liquid aromatic hydrocarbons fed to the rectification column and a connected unit for adjusting the flow rate of feedstock components fed to the mixer and/or adjusting the temperature of the rectification column.

These advantageous characteristics make it possible to improve the efficiency of AHCC production and increase the concentration of alkylbenzenes, in particular xylenes. In fact, the possibility of measuring the composition of liquid aromatic hydrocarbons and controlling the process are all aimed at increasing the useful product at the output.

A variant of the invention exists in which the installation additionally includes a unit for separating undesirable diene and aromatic olefin oligomerization products (tars), located in the heating unit after the evaporator of feedstock with boiling points below 250° C. under normal conditions and before the reheater of the mixture to the temperature at which the mixture is fed to the reactor, whose first input is connected to the output of the mixture heater, whose first output is connected to the mixture reheater, and the second output is the output for tar removal.

This advantageous characteristic makes it possible to separate and remove undesirable tars.

A variant of the invention exists in which the unit for measuring the composition of liquid aromatic hydrocarbons is made in the form of an on-stream chromatograph.

This advantageous characteristic makes it possible to measure the composition of liquid aromatic hydrocarbons using a precise and tested device.

The combination of essential features of the claimed invention is unknown from the technological level for installations with similar purposes, which supports the conclusion that the invention as an installation meets the novelty criterion.

BRIEF DESCRIPTION OF THE DRAWINGS

Other distinguishing features and advantages of the invention clearly follow from the specification presented below, which is for illustration and not restrictive, with references to the attached figures, in which.

Figure 1:
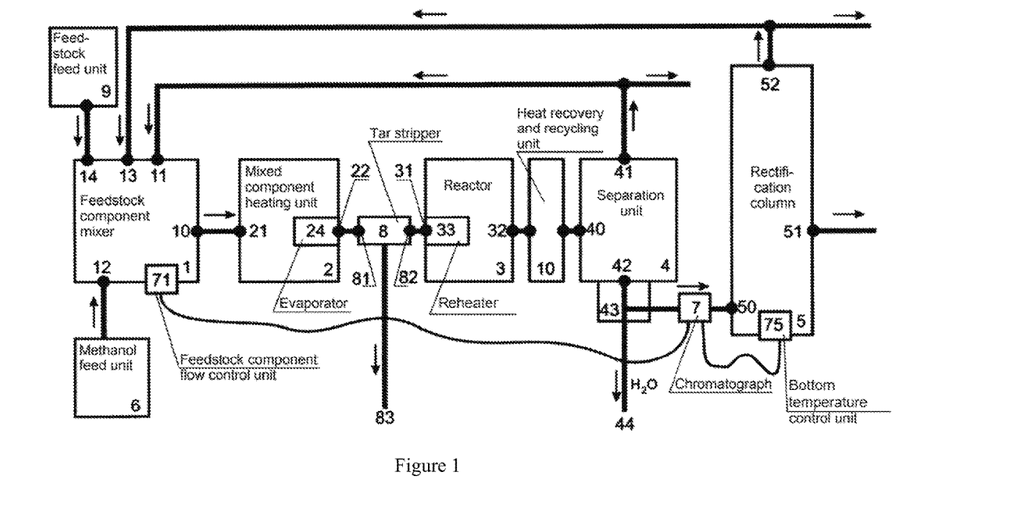
FIG. 1 schematically depicts the layout of the installation for producing AHCC from liquid hydrocarbon fractions according to the invention.

According to FIG. 1, the installation for producing AHCC from liquid hydrocarbon fractions includes feedstock component mixer 1, whose output 10 is connected to input 21 of mixed component heating unit 2, whose output 22 is connected to input 31 of reactor 3, in which the heated components undergo conversion in the presence of a catalyst to aromatic hydrocarbons. Reactor 3 ensures nearly isothermal conversion of hydrocarbons. Output 32 of reactor 3 through heat recovery and recycling unit 10 (the heat is used to evaporate the mixture, heat the bottom of the column, heat the coolant used to condense liquid hydrocarbons in the conversion product) is connected to input 40 of unit 4 for separating resulting product into liquid and gaseous phases. The first, gas-phase, output 41 of unit 4 is connected to the first input 11 of feedstock component mixer 1. Its second, liquid-phase, output 42 is connected to input 50 of rectification column 5, from whose first output 51 the AHCC is collected.

Feedstock component mixer 1 has second input 12 for methanol feed, adapted for connection to methanol feed unit 6. Unit 6 is not part of the installation.

Feedstock component mixer 1 has third input 14 for hydrocarbon feed, adapted for connection to hydrocarbon feed unit 9. Unit 9 is not part of the installation.

Rectification column 5 has second output 52 for components remaining after AHCC collection, connected to third input 13 of feedstock component mixer 1. Components may be collected via output 52 either in the gaseous or the liquid and gaseous phases.

Liquid-gas separator unit 4 additionally has module 43 for separating the liquid phase into liquid hydrocarbons and water, connected to input 50 of rectification column 5, and having water removal output 44.

The installation additionally includes unit 7 for measuring the composition of aromatic hydrocarbons fed to rectification column 5. Unit 7 is connected to unit 71 for adjusting the flow rate of feedstock components fed to the mixer and/or unit 75 for adjusting the temperature of the rectification column (bottom).

The installation may additionally include tar separation unit 8, located after evaporator 24 which evaporates feedstock with boiling points below 250° C. under standard conditions, located in unit 2 and before reheater 33 which reheats the mixture to the temperature at which the mixture is fed to the reactor 3, located in reactor 3. The first input 81 of unit 8 is connected to mixture evaporator 24, and the first output 82 of unit 8 is connected to mixture reheater 33, while the second output 83 is the tar removal output.

Tar separation unit 8, the tar separator, may be made on the basis of a centrifugal separator.

Aromatic hydrocarbon composition measuring unit 7 can be made in the form of an on-stream chromatograph.

Here, the "reaction zone" of reactor 3 means the entire reactor space in which hydrocarbon conversion occurs, including the space divided into separate segments. Reactor 3 may be a multi-bed type, for example, with mixing of flows within the reactor. It may have several feedstock mixing and supply zones. The reactor may also be tubular, with charging catalyst to the reaction tubes, etc.

During the conversion of hydrocarbons to AHCC, fixed-bed reactors with periodic catalyst regeneration or fluidized-bed catalytic reactors with continuous catalyst regeneration may be used.

The claimed device and method of embodiment predominantly employs a catalyst that contains a pentasil-type zeolite with a silicate modulus $SiO_2/Al_2O_3$=40-50, pretreated with an aqueous alkali solution modified by lanthanum oxide in a quantity of 0.5-2.0% by weight, as well as a binder in a quantity of 20-25% by weight of the catalyst weight. As the binder, alumina and/or silica are preferred. If an oxide mixture is used, the concentration of silica in the mixture may vary from 0.1% to 99.9% by weight. The distinguishing feature of the method is that the aluminosilicate catalyst simultaneously possesses activity in the aromatization and alkylation of lower aromatic hydrocarbons (benzene, toluene, etc.) by $C_2$-$C_4$ olefins formed (in situ) during the transformation of oxygenates.

"Water" means water that may contain residual hydrocarbons and oxygenates.

EMBODIMENT OF THE INVENTION

The production of AHCC according to the invention is carried out as follows.

Figure 2:
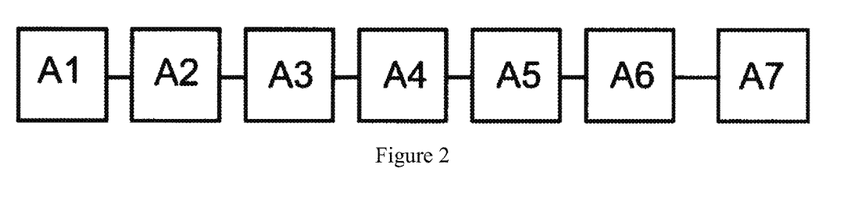
FIG. 2 schematically depicts the steps of the method of producing aromatic hydrocarbon concentrate from liquid hydrocarbon fractions according to the invention.

Step A1. Hydrocarbons for conversion, as well as recycle products, are fed to feedstock component mixer 1 at a pressure of 1-4 MPa. There they are mixed with methanol fed from methanol feed unit 6 in a ratio at which the methanol makes up 20-70% of the mixture by weight.

Step A2. Then the mixture is fed to mixed component heating unit 2, where methanol and hydrocarbons with boiling points below 250° C. under normal conditions evaporate. Heating achieves 100% homogenization of the mixture.

Step A3. Optionally, the mixture is fed to tar separation unit 8, for which a centrifugal separator may be used. From tar separation unit 8, tar is removed, while the gas-phase mixture is fed to reactor 3 and thence to heat recycling unit 10, in which the conversion product is cooled to condense liquid hydrocarbons and water.

Step A4. The reaction product is fed to liquid-gas separator unit 4, which also has liquid hydrocarbonwater separator module 43. The water is removed. The gaseous phase is partly recycled to feedstock component mixer 1.

Step A5. The remaining hydrocarbon mixture is fed to rectification column 5. There, the mixture is separated into fractions.

At least part of the hydrocarbon components remaining in the rectification column after removal are fed to feedstock component mixer 1, and the AHCC is removed.

Step A6. The composition of liquid aromatic hydrocarbons fed to rectification column 5 is measured, and based on the results of measurement of the composition of liquid aromatic hydrocarbons, the ratio between the feedstock components fed to mixer 1 is adjusted with the aid of unit 71 and/or the temperature of rectification column 5 is adjusted with the aid of unit 75.

Aromatic hydrocarbon composition measuring unit 7 compares information on the current and required ratio of the concentration of benzene to the total aromatic hydrocarbon concentration by weight. If the ratio of the benzene concentration to the total aromatic hydrocarbon concentration in the product is too high or too low, the unit, based on the comparison, issues a control action to units 71 and 75.

The sequence of steps is illustrative and permits some operations to be reordered, added, or performed simultaneously without loss of the capability of producing AHCC from liquid hydrocarbon fractions.

INDUSTRIAL APPLICABILITY

The claimed installation for producing aromatic hydrocarbon concentrate from liquid hydrocarbon fractions may be embodied in practice, and when embodied it affords realization of the claimed purpose, which supports the conclusion that the invention meets the industrial applicability criterion.

In accordance with the claimed invention, tests and calculations of the production of aromatic hydrocarbon concentrate from liquid hydrocarbon fractions have been performed.

Measurements and calculations have revealed the following:

The high aromatic hydrocarbon yield (in the prototype, the aromatic hydrocarbon yield is 82-83% of its concentration in the feedstock) in the claimed method is 150-160% by weight of the total aromatic hydrocarbons in the feedstock. Accordingly, less $C_1$-$C_4$ light hydrocarbons were produced.

Natural gas is involved indirectly as feedstock via methanol, which is generally produced from natural gas.

In conversion with methanol, feedstock containing dienes and aromatic olefins prone to tar formation may be used inter alia. An example of such feedstock may be low-sulfur "crude" (unhydrogenated) pyrolysis condensate (liquid pyrolysis products).

The methanol concentration in the feedstock for conversion may be used to adjust the component composition of the resulting aromatic hydrocarbon concentrate.

With an equal volumetric methanol/hydrocarbon ratio, the process using pyrolysis condensate proceeds with better indicators of aromatic hydrocarbon concentrate yield to the initial pyrolysis condensate. So at a volumetric methanol/hydrocarbon ratio of one, the aromatic hydrocarbon concentrate yield was 120.7% by weight versus 116% by weight when selectively olefin-hydrogenated pyrolysis condensate was used.

A substantial increase was recorded in the total aromatic hydrocarbon concentration for the fraction IBP-FBP (initial boiling point-final boiling point) from 70-75% to 88-90% by weight when "crude" or selectively hydrogenated pyrolysis condensate was converted. The aromatic hydrocarbon concentration of the 150° C.-FBP fraction is as high as 98%.

A substantial reduction in olefins in liquid hydrocarbon fraction of the conversion product (residual concentration ~0.5%) was recorded.

A substantial reduction in the concentration of saturated hydrocarbons in the conversion products of both selectively hydrogenated and "crude" pyrolysis condensates was recorded. Thus the concentration of cycloparaffins in the conversion product of selectively (olefin-)hydrogenated pyrolysis condensate declined from 8.4% to 0.5%. The concentration of paraffins in the conversion products in samples of pyrolysis condensates declined from 15-17% to 7%, which supports the conjecture of cracking and dehydrocyclization of saturated hydrocarbons.

An increase in the ratio of total methyl groups to total phenyl groups in the liquid conversion product to 1.5-1.7 was recorded, which supports the claim of expected increase in xylene yield in subsequent refining of the liquid conversion product using transalkylation technology.

Figure 3:
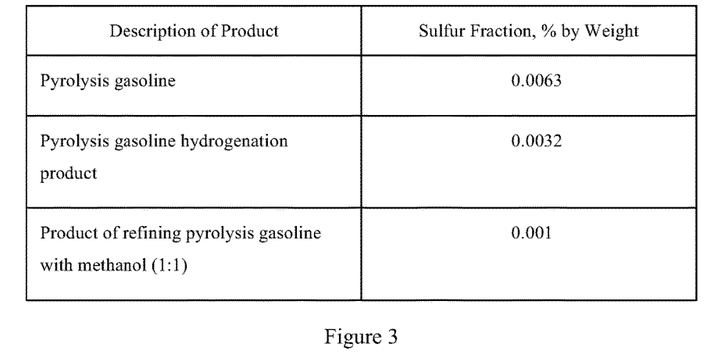
FIG. 3 shows the table, "Change in Sulfur Content in the Products of Hydrogenation and Refining of Pyrolysis Gasoline" according to the invention.

A sixfold reduction in the concentration of sulfur compounds due to conversion of sulfur compounds to hydrogen sulfide was recorded. A comparison of the sulfur contents of the feedstock and conversion product is tabulated in FIG. 3.

In composition, the end gas of the process is natural gas liquids containing 55-60% propane and 12-15% olefins, and is a valuable chemical feedstock, for example for pyrolysis.

An increase in the efficiency of alkylbenzene concentrate production, when the ratio of the aromatic hydrocarbon yield to the initial hydrocarbon fraction reaches 120%, but this occurs with substantially less gas formation, and with a reduction in catalyst costs due to their possible lack of noble metal content.

Figure 4:
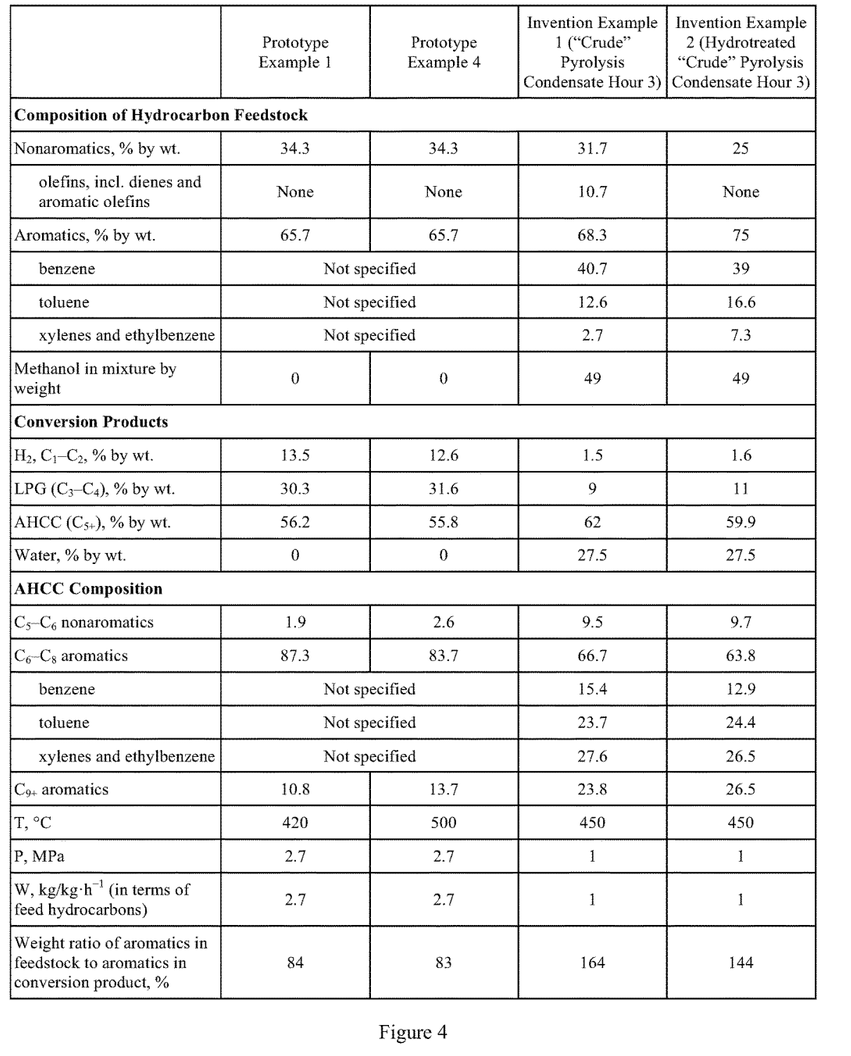
FIG. 4 shows the table, "Comparison of Parameters of the Composition of Feed Hydrocarbons and Conversion Products in the Prototype and According to the Invention."

A comparison of parameters of the composition of hydrocarbon feedstock and conversion products in the prototype and according to the invention is tabulated in FIG. 4.

Thus, this invention achieves its stated objective of improving the efficiency of aromatic hydrocarbon concentrate production and increasing the concentration of alkylbenzenes, in particular xylenes.

The invention claimed is:

1. A method of producing aromatic hydrocarbon concentrate from liquid hydrocarbon fractions, in which feedstock components are fed to a mixer to thereby provide mixed components, the mixed components are heated, the mixed components are fed to a reactor in which the heated components undergo conversion in the presence of a zeolite catalyst to a resulting product comprising aromatic hydrocarbons, the resulting product is separated into liquid and gaseous phases, at least part of the gaseous phase is fed to the mixer, the liquid phase is fed to a rectification column, from which aromatic hydrocarbon concentrate is collected, characterized in that:
 a) methanol is additionally fed to the mixer,
 b) the mixed components are heated until they fully homogenize in the gaseous phase,
 c) at least part of the hydrocarbon components remaining in the rectification column after collection are fed to the mixer,
 d) the liquid phase is additionally separated into liquid hydrocarbons and water, and the liquid hydrocarbons are fed to the rectification column while the water is diverted,
 e) the composition of liquid aromatic hydrocarbons fed to the rectification column is measured, and based on the results of measurement of the liquid aromatic hydrocarbon composition, the ratio between the feedstock components fed to the mixer and/or the temperature of the rectification column bottom is adjusted.

2. Method according to claim 1, characterized in that methanol is fed to the mixer to produce a mixture in which methanol makes up 20-70% by weight.

3. Method according to claim 1, characterized in that when the composition of liquid aromatic hydrocarbons fed to the rectification column is measured, the concentration of benzene and the concentration of total aromatic hydrocarbons, consisting primarily of methylbenzenes, is determined, and if the ratio of benzene concentration to the total aromatic hydrocarbon concentration rises or falls, the flow rates of feedstock components fed to the mixer and/or the temperature of the rectification column are adjusted so that the benzene concentration by weight relative to the total aromatic hydrocarbon concentration by weight in the hydrocarbons collected from the rectification column falls within the range of 8-30%.

4. Method according to claim 1, characterized in that adjustment of the flow rate of feedstock components fed to the mixer is effected by altering the methanol flow rate.

5. Method according to claim 1, characterized in that adjustment of the flow rate of feedstock components fed to the mixer is effected by altering the hydrocarbon fractions flow rate.

6. Method according to claim 1, characterized in that after the mixed components are heated to a temperature at which hydrocarbons boiling at 250° C. under standard conditions preferentially evaporate, products of radical oligomerization of dienes and aromatic olefins present in the feedstock are separated using a centrifugal separator-tar stripper.

7. Method according to claim 1, characterized in that measurement of the composition of liquid aromatic hydrocarbons is effected using an on-stream chromatograph.

8. Installation for producing aromatic hydrocarbon concentrate from liquid hydrocarbon fractions, including a feedstock component mixer whose output is connected to the input of a mixed component heating unit, whose output is connected to the input of a reactor in which heated components are converted in the presence of a catalyst to aromatic hydrocarbons, whose output is connected to the input of a unit for separating the resulting product into liquid and gaseous phases, the first gaseous phase output of which is connected to the first input of the feedstock component mixer, and whose second liquid phase output is connected to the input of a rectification column, from whose first output aromatic hydrocarbon concentrate is collected, characterized in that
 a) the feedstock component mixer has a second input for feeding methanol, adapted for connection to a methanol feed unit,
 b) the rectification column has a second output for components remaining after collection of aromatic hydrocarbon concentrate, connected to the third input of the feedstock component mixer,
 c) the liquid-gas separator unit additionally has a module for separating the liquid phase into liquid hydrocarbons and water, which is connected to the input of the rectification column and has an output for removal of water, d) the installation additionally includes a unit for measuring the composition of the liquid aromatic hydrocarbons that are fed to the rectification column and a connected unit for adjusting the flow rate of feedstock components fed to the mixer and/or a unit for adjusting the temperature of the rectification column.

9. Installation according to claim 8, characterized in that the installation additionally includes a tar separation unit located after the evaporator of feedstock components boiling under standard conditions at a temperature of 250° C. located in the heating unit and before the reheater of the mixture to the temperature at which the mixture is fed to the reactor, which reheater is located in the reactor, the first input of the tar separation unit is connected to said mixture heater, the first output of the tar separation unit is connected to the mixture reheater, and the second output of the tar separation unit is the output for removal of tar.

10. Installation according to claim 8, characterized in that the unit for measuring the composition of liquid aromatic hydrocarbons is made in the form of a on-stream chromatograph.

* * * * *